United States Patent
Sawamura et al.

(12)

(10) Patent No.: US 6,987,126 B2
(45) Date of Patent: Jan. 17, 2006

(54) NEUTRALIZING AGENT FOR CLOSTRIDIUM BACTERIAL NEUROTOXINS AND PREPARATION METHOD THEREOF

(75) Inventors: Shin-ichi Sawamura, Haibara-gun (JP); Masakazu Nishimura, Obihiro (JP); Iwao Sakane, Haibara-gun (JP)

(73) Assignee: Ito En, Ltd., Tokyo (JP)

( * ) Notice: Subject to any disclaimer, the term of this patent is extended or adjusted under 35 U.S.C. 154(b) by 169 days.

(21) Appl. No.: 10/702,638

(22) Filed: Nov. 7, 2003

(65) Prior Publication Data

US 2004/0102387 A1 May 27, 2004

(30) Foreign Application Priority Data

Nov. 7, 2002 (JP) .......................... 2002-324223

(51) Int. Cl.
 A61K 31/353 (2006.01)
 C07D 311/30 (2006.01)

(52) U.S. Cl. ....................... 514/456; 549/403

(58) Field of Classification Search ............... 514/456; 549/403
 See application file for complete search history.

(56) References Cited

FOREIGN PATENT DOCUMENTS

| EP | 0 397 914 | 11/1990 |
|----|-----------|---------|
| EP | 1 236 724 | 9/2002 |
| JP | 2-276562 | 11/1990 |
| JP | 2-304079 | 12/1990 |
| JP | 2-306915 | 12/1990 |
| WO | WO 01/40213 | 6/2001 |

OTHER PUBLICATIONS

Eiki Satoh, et al., "Black Tea Extract, Thearubigin Fraction, Counteract the Effects of Botulinum Neurotoxins in Mice", British Journal of Pharmacology, vol. 132, 2001, pp. 797–798.

Eiki Satoh, et al., "Black Tea Extract, Thearubigin Fraction, Counteracts the Effect of Tetanus Toxin in Mice", Exp. Biol. Med., vol. 226, No. 6, 2001, pp. 577–580.

Eiki Satoh, et al., "The Mechanism Underlying the Protective Effect of the Thearubigin Fraction of Black Tea (*Camellia Sinensis*) Extract Against the Neuromuscular Blocking Action of Botulinum Neurotoxins", Pharmacology & Toxicology, vol. 90, 2002, pp. 199–202.

(Continued)

*Primary Examiner*—Taofiq Solola
(74) *Attorney, Agent, or Firm*—Oblon, Spivak, McClelland, Maier & Neustadt, P.C.

(57) ABSTRACT

Disclosed is a neutralizing agent for a *clostridium* bacterial neurotoxin and a preparation method thereof. The neutralizing agent contains a flavonol glycoside (A) or a flavonol glycoside (B). The flavonol glycoside (A) has a flavone skelton which has two hydroxyl groups at the 5 and 7 positions, at least one hydroxyl group bonding at either one of the 3', 4' and 5' positions, and an ether linkage forming glycoside at the 3 position with a carbohydrate chain containing a rutinose skelton. The flavonol glycoside (B) has also another ether linkage at the 4' position with a carbohydrate chain containing rhamnose. The neutralizing agent is prepared by separating the thearubigin fraction of black tea extract by elution with methanol/water solvent using a reverse phase liquid chromatography. A fraction eluted with methanol/water solvent containing 40% methanol and a fraction eluted with methanol/water solvent containing 60% methanol have high neutralizing activity, and at least one of them is collected.

11 Claims, 1 Drawing Sheet

OTHER PUBLICATIONS

Eiki Satoh, et al., "A Mechanism of the Thearubigin Fraction of Black Tea (*Camellia Sinensis*) Extract Protecting Against the Effect of Tetanus Toxin", The Journal of Toxicological Sciences, vol. 27, No. 5, 2002, pp. 441–447.

Database Embase 'Online!, EMB–2002439528, XP–002270983, 2000.

A. H. Brantner, et al., Journal of Ethnopharmacology, vol. 66, No. 2, XP–002270981, pp. 175–179, "Quality Assessment of Paliurus Spina–Christi Extracts", 1999.

Y.–Y. Mo, et al., Plant Physiology, vol. 107, No. 2, XP–002270982, pp. 603–612, "Analysis of Sweet Cherry (Prunus Avium L.) Leaves for Plant Signal Molecules that Activate the Syrb Gene Required for Synthesis of the Phytotoxin, Syringomycin, by Pseudomonas Syringae PV Syringae", 1995.

H. Itokawa, et al., Phytochemistry, vol. 20, No. 10, XP–001179712, pp. 2421–2422, "Flavonol Glycosides from the Flowers of Cucurbita Pepo", 1981.

NEUTRALIZING AGENT FOR CLOSTRIDIUM BACTERIAL NEUROTOXINS AND PREPARATION METHOD THEREOF

BACKGROUND OF THE INVENTION

1. Field of Invention

The present invention relates to a neutralizing agent for *clostridium* bacterial neurotoxins and a preparation method thereof, and in particular, relates to a *clostridium* bacterial neurotoxin-neutralizing agent which can be added to food without affecting its flavor, to neutralize *clostridium* bacterial neurotoxins and protect from poisoning, and a preparation method of the *clostridium* bacterial neurotoxin-neutralizing agent.

2. Related Art

*Clostridium botulinum* is known to be the bacterium responsible for the mass food poisoning caused by Izushi (fermented Japanese food made from a mixture of fish, rice and vegetables) or Karashi-renkon (fried Japanese food made from lotus root) in the past in Japan, and also caused by ham, bottled food, etc. in the U.S. and Europe. This food poisoning is toxicosis due to oral intake of neurotoxins produced by the bacterium in food, rather than *botulinum* infection. *Botulinum* neurotoxin produced by *botulinum* is known to be the most potent neurotoxin to mammals owing to its high lethality. The neurotoxins are classified serologically into seven types (BoNT/A to G), and the process of the toxic action consists of the following three steps:

1) Binding of the toxic protein to the cell surface of presynaptic nerve terminal;
2) Internalization into cells; and
3) Proteolysis of the target protein by an endopeptidase activity present in the proteolytic domain.

Botulism can be treated with an antiserum therapy by administration of the antiserum. However, it is desirable to prevent before being affected by the poisoning, and the current method for prevention of the poisoning is to inhibit the bacterial growth and proliferation by means of sterilization of food by heating.

On the other hand, food that has been confirmed for the occurrence of botulism includes processed food such as ham, vacuum-packed food or bottled food, "Narezushi" (lactic acid fermented Japanese food) such as Izushi or Funazushi (a kind of fermented sushi made with fresh water fish), and the like, and it is obvious that there are difficult cases where sufficient sterilization can not be assured by heat sterilization. Therefore, search for substances to neutralize the neurotoxins is being conducted.

Under the above circumstances, it has become apparent that black tea extract contains *botulinum* neurotoxin-neutralizing substances, which have been found to be present in thearubigin fraction obtained by crude fractionation of black tea extract (refer to the references (1) and (2) below).

(1) Satoh E, Ishii T, Shimizu Y, Sawamura S and Nishimura M, "Black tea extract, thearubigin fraction, counteract the effects of *botulinum* neurotoxins in mice", *Br. J. Pharmacol.*, 132, 797–798(2001)

(2) Satoh E, Ishii T, Shimizu Y, Sawamura S and Nishimura M, "The mechanism underlying the protective effect of the thearubigin fraction of black tea (*Camellia sinensis*) extract against the neuromuscular blocking action of *botulinum* neurotoxins", *Pharmacol Toxicol,* 90, 199–202(2002)

Thearubigin in black tea is a generic name for brown-colored acidic pigments fraction of black tea extract, which contains many substances besides those neutralizing the toxin and is effective in respect of neutralizing *botulinum* neurotoxins by being added to food.

However, when the thearubigin fraction of black tea is added to raw ham and the like, protein coagulation is brought about, showing "distasteful", "astringent" and "bitter" tastes in the organoleptic test. Accordingly, it is necessary to identify the toxin-neutralizing substances in the thearubigin fraction of black tea and to purify the thearubigin fraction so as not to damage the flavor of food.

SUMMARY OF THE INVENTION

It is an object of the present invention to provide a *clostridium* bacterial neurotoxin-neutralizing agent which can be added to food without damage to the flavor and a method of preparation thereof.

To achieve the above object, according to one aspect of the present invention, the neutralizing agent for a *clostridium* bacterial neurotoxin comprises: at least one of a flavonol glycoside (A) and a flavonol glycoside (B), the flavonol glycoside (A) having a flavone skelton which has two hydroxyl groups at the 5 and 7 positions, at least one hydroxyl group bonding at either one of the 3', 4' and 5' positions, and an ether linkage forming glycoside at the 3 position with a carbohydrate chain containing a rutinose skelton, and the flavonol glycoside (B) having a flavone skelton which has two hydroxyl groups at the 5 and 7 positions, an ether linkage forming glycoside at the 4' position with a carbohydrate chain containing a rhamnose skelton, and an ether linkage forming glycoside at the 3 position with a carbohydrate chain containing a rutinose skelton.

The above flavonol glycoside (A) includes at least one component selected from the group consisting of rutin, nicotiflorin and kaempfetrin.

In addition, according to one aspect of the present invention, the method for preparing a neutralizing agent for a *clostridium* bacterial neurotoxin comprises: separating the thearubigin fraction of black tea extract by elution with methanol/water solvent using a reverse phase liquid chromatography; and collecting a fraction eluted with methanol/water solvent containing 40% methanol and/or a fraction eluted with methanol/water solvent containing 60% methanol.

Further, according to another aspect of the present invention, the method for preparing a neutralizing agent for a *clostridium* bacterial neurotoxin comprises: purifying the thearubigin fraction of black tea extract by elution separation of the thearubigin fraction with methanol/water solvent using the reverse phase liquid chromatography.

According to one aspect, the present invention provides a flavonol glycoside having a chemical structure which is expressed by the structural formula (2) illustrated hereafter, where -rha represents a rhamnosyl group, and -glc-rha represents a rutinosyl group.

BRIEF DESCRIPTION OF THE DRAWING

The features and advantages of the neutralizing agent for a *clostridium* bacterial neurotoxin will be more clearly understood from the following description of the preferred embodiments of the present invention taken in conjunction with the accompanying drawings in which.

DETAILED DESCRIPTION OF THE INVENTION

Figure 1:
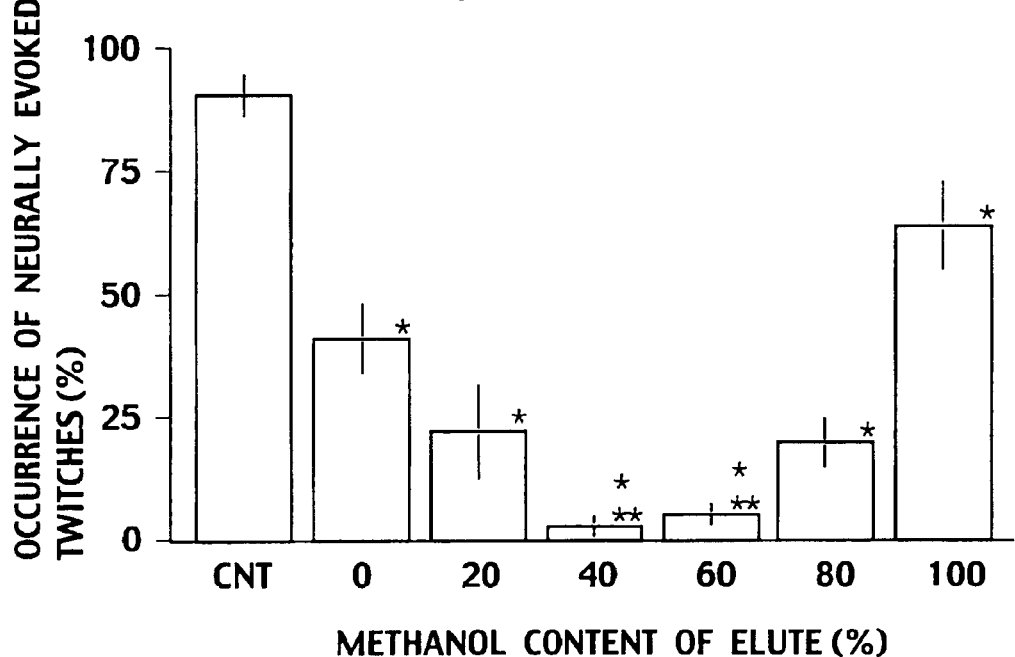
FIG. 1 is a graph showing the ratio of occurrence of neurally evoked twitches observed for each eluate obtained by HPLC elution separation of thearubigin fraction of black tea using methanol/water.

Thearubigin fraction of black tea is an alcoholic extract from water or hot water extract of black tea leaves and a generic name for brown-colored acidic pigments fraction. Referring to the fractionation specifically, caffein fraction (chloroform extract) and catechin and theaflavin fraction (ethyl acetate extract) are extracted and removed from the hot water extract of black tea leaves, before obtaining the thearubigin fraction as an extract with n-butanol, which belongs to tannins in black tea. The main flavonoids present in black tea are contained in the ethyl acetate extract, many alkaloids are contained in the chloroform extract, and amino acids are contained in the aqueous phase. The effect of neutralizing bacterial neurotoxins by the thearubigin fraction is exerted by inhibition of binding of the neurotoxins to cell surface.

In order to identify the bacterial toxin-neutralizing substance, study has been conducted on purification of the thearubigin fraction by the inventors of the present application. As a result, it has been confirmed that the thearubigin fraction can be further purified into fractions being higher in the toxin-neutralizing activity, by means of elution separation of the thearubigin fraction on a reverse phase HPLC column using methanol-water solvent system (methanol content: 0%, 20%, 40%, 60%, 80% and 100%). Moreover, fifteen components have been possibly isolated from the separated eluates. The result of measurements of these components in the neutralizing activity against *botulinum* neurotoxins shows that the first, second, third and fourth components in the order of elution among the five components obtained from the 60% methanol eluate have high activities. Molecular structures of these four components are elucidated by their NMR spectra; the first component is rutin (quercetin-3-O-glc-(6-1)-rha, the compound of the structural formula (1) below) that is one of quercetin glycosides, the second component is kaempferol-3-(O-glc-rha)-4'-O-rha (the structural formula (2) below), the third component is kaempfetrin (kaempferol-3-O-glc-(6-1)-rha-(3-1)-glc, the compound of the structural formula (3) below), the fourth component is nicotiflorin (kaempferol-3-O-glc-(6-1)-rha, the compound of the structural formula (4) below), and the second, third and fourth components are kaempferol glycosides. These four components do not give a bitter taste like tannin or flavor-damaging tastes, and the 60% methanol eluate containing these components also does not give a flavor-damaging taste, and therefore, the purified substances obtained by purification of the thearubigin fraction can provide food with a neutralizing activity against the bacterial neurotoxin without damaging food flavor. There are also other defined components which are not so high in the toxin-neutralizing activity in comparison with the above four components. They are all flavonol glycosides each of which possesses a flavone skeleton having two hydroxyl groups at the 5 and 7 positions and at least one hydroxyl group bonded to either of the 3', 4' and 5' positions, and also having an ether linkage forming glycoside at the 3 position with a carbohydrate chain containing a rutinose (i.e. glucose-rhamnose) skeleton. They are considered to also contain, for example, myricetin glycoside and the like, but have not been confirmed by isolation.

(glc: glucosyl, rha: rhamnosyl)

In the test of neutralizing activity against the *clostridium* bacterial neurotoxin, the 40% methanol eluate also shows the activity and it does not give a flavor-damaging taste. Therefore, this fraction can also be used for food as a neutralizing agent for the bacterial neurotoxins. The fraction in which 40% methanol eluate and 60% methanol eluate are fractionated together has a sufficient activity as the bacterial neurotoxin-neutralizing agent, and it also does not damage flavor as a food additive. Therefore, in view of the efficiency of preparation, it is preferable to fractionate the 40% methanol eluate and 60% methanol eluate together. Thus, eluates to be fractionated may be adjusted in accordance with the desired activity. If a neutralizing agent with higher activity against the bacterial toxin is desired to be prepared, only the 60% methanol eluate may be fractionated, and if further higher activity is required, the above four components, (1) to (4), can be separately fractionated.

For more efficient preparation of the neutralizing agent for the bacterial neurotoxins, it is effective for the extraction of black tea leaves to be carried out with an aqueous solution of 80% acetone in place of water or hot water. The extraction with aqueous acetone can extract more components from black tea compared to that with water, and the thearubigin fraction is obtained by partition extraction of the black tea extract dispersed in water with n-butanol after chloroform and ethyl acetate extractions. It can be excellently separated on the reverse phase HPLC column using methanol-water solvent system as in the case of the water extract. The amount of components extractable from black tea with a different concentration of aqueous acetone is reduced in comparison with that with 80% aqueous acetone solution, but its extractable amount is still larger than that with water. Further, in the preparation of thearubigin fraction, the consistency of fractionating thearubigin fraction from the extract is improved by performing n-hexane extraction prior to the chloroform extraction.

The thearubigin fraction of black tea extract shows anti-toxin activity against the neurotoxins of *Clostridium tetani* which belongs to the same *Clostridium* as *botulinum*, and the above four components (a quercetin glycoside and kaempferol glycosides) are also effective as neutralizing agents for the neurotoxins common to *Clostridium* species of bacteria.

In recent years, *botulinum* neurotoxins have been used for a treatment method alternative to surgical therapy for a variety of spastic paralyses such as blepharospasm and facial spasm. Accordingly, the bacterial neurotoxin-neutralizing agents of the present invention can also be used as an agent for adjusting the toxicity of the above therapeutic agent for the spastic paralysis. In this case, the agents separated and purified from thearubigin fraction up to the above four components are most suitable, and a diluent which does not affect a living body may be used to control the neutralizing activity against toxins.

EXAMPLES

To 500 g of black tea was added 3 L of 80% aqueous acetone solution and extracted for 12 hours at room temperature. This procedure was carried out twice and the two extracts obtained by solid-liquid separation were combined together, concentrated under vacuum and freeze-dried to yield 330 g of a crude extract of black tea. The obtained crude extract was dispersed in 1.5 L of distilled water and extracted in turn by partition with 6 L of hexane, 6 L of chloroform, 6 L of ethyl acetate and 6 L of n-butanol, and each organic solvent phase was recovered, concentrated and freeze-dried to yield 19.4 g of n-hexane-soluble part, 50.6 g of chloroform-soluble part, 95 g of ethyl acetate-soluble part and 60.3 g of n-butanol-soluble part (thearubigin fraction). The water-soluble part was 64.5 g.

When the bacterial neurotoxin-neutralizing activity of each solvent-soluble part was examined according to the measurement method described below, a high activity was observed in the n-butanol-soluble part.

The above n-butanol-soluble part was separated by elution from a reverse phase HPLC column (Shiseido CapcellPak, inner diameter 5 cm, length 10 cm) using methanol-water solvent system (methanol content: 0%, 20%, 40%, 60%, 80% and 100%). The amount of constituent part contained in each eluate was: 2.5 g (in water eluate), 14.1 g (in 20% methanol eluate), 22 g (in 40% methanol eluate), 4.1 g (in 60% methanol eluate), 3.0 g (in 80% methanol eluate), and 1.2 g (in 100% methanol eluate). Using each of the eluted parts as a sample, the examination of toxin-neutralizing activity of each eluted part (expressed as a ratio of occurrence of neurally evoked twitches in the graph) yielded the results shown in the graph of FIG. 1, where a strong neutralizing activity against the bacterial neurotoxin was found in the 40% methanol-eluted part (yield, 22 g) and 60% methanol-eluted part (yield, 4.1 g) ("CNT" in the graph indicates the control, and the vertical bars show standard errors. The attached star marks show the results of significant tests, with one mark indicating 10% significant difference and two marks being 5%). Upon separation of each of these eluted parts on the reverse phase HPLC column (the same as the above) using 30% ethanol-0.1% acetic acid as eluant, nine components and five components were isolated, respectively, from the 40% methanol-eluted part and the 60% methanol-eluted part, and each of these components was tried to define its molecular structure by NMR analysis. As a result, for the first, second, third and fourth eluted components of the 60% methanol-eluted part, NMR spectra were possibly measured with a NMR spectrometer (trade name: α-400, manufactured by JEOL Ltd. of Japan), and the data shown in Table 1 and Table 2 were obtained. The molecular structures were determined based on these data, identifying that the first component was rutin of the formula (1); the second component was a kaempferol compound of the formula (2); the third component was kaempfetrin of the formula (3); and the fourth component was nicotiflorin of the formula (4). Each of these four components was measured for its neurotoxin-neutralizing activity, and they were confirmed to have high toxin-neutralizing activities, individually, as shown in FIG. 2. FIG. 2 shows the neuromuscular contractility for each of the eluted components, i.e. the first component (60-1), the second component (60-2), the third component (60-3) and the fourth component (60-4) derived from the 60% methanol eluate. The neuromuscular contractility shows the ability of autonomic contraction held against neuroparalysis caused by toxication at the time when that for the control sample is reduced to 50%. For the other components in 40% methanol eluate, definition of molecular structure was difficult due to the lack of yielded mass, etc.

TABLE 1

| | $^{1}H$ NMR data 1, 2, 3, 4 | | | |
|---|---|---|---|---|
| | 1st | 2nd | 3rd | 4th |
| 6 | 6.20(d,J = 2 Hz) | 6.73(d,J = 2 Hz) | 6.23(d,J = 2 Hz) | 6.21(d,J = 2 Hz) |
| 8 | 6.43(d,J = 2 Hz) | 6.43(d,J = 2 Hz) | 6.47(d,J = 2 Hz) | 6.43(d,J = 2 Hz) |
| 2' | 7.66(d,J = 2 Hz) | 8.15(d,J = 9 Hz) | 8.08(d,J = 9 Hz) | 8.06(d,J = 9 Hz) |
| 3' | — | 7.15(d,J = 9 Hz) | 6.93(d,J = 9 Hz) | 6.89(d,J = 9 Hz) |
| 5' | 6.90(d,J = 8 Hz) | 7.15(d,J = 9 Hz) | 6.93(d,J = 9 Hz) | 6.89(d,J = 9 Hz) |
| 6' | 7.58(dd,J = 8.2 Hz) | 8.15(d,J = 9 Hz) | 8.08(d,J = 9 Hz) | 8.06(d,J = 9 Hz) |
| $1^{I}$ | 5.05(d,J = 7.5 Hz) | 5.13(d,J = 7.5 Hz) | 5.11(d,J = 7.5 Hz) | 5.10(d,J = 8 Hz) |
| $2^{I}$ $3^{I}$ $4^{I}$ $5^{I}$ | 3.4~3.8(m) | 3.4~3.8(m) | 3.4~3.8(m) | 3.4~3.8(m) |

TABLE 1-continued $^1$H NMR data 1, 2, 3, 4

| | 1st | 2nd | 3rd | 4th |
|---|---|---|---|---|
| $6^I$ | | | | |
| $1^{II}$ | 4.50(d,J = 1.5 Hz) | 4.47(d,J = 1.5 Hz) | 4.53(d,J = 1.5 Hz) | 4.53(d,J = 1.5 Hz) |
| $2^{II}$ | | | | |
| $3^{II}$ | | | | |
| $4^{II}$ | 3.4~3.8(m) | 3.4~3.8(m) | 3.4~3.8(m) | 3.4~3.8(m) |
| $5^{II}$ | | | | |
| $6^{II}$ | 1.03(d,J = 6 Hz) | 1.10(d,J = 8 Hz) | 1.07(d,J = 8 Hz) | 1.10(d,J = 8 Hz) |
| $1^{III}$ | | | 4.40(d,J = 7.5 Hz) | |
| $2^{III}$ | | | | |
| $3^{III}$ | | | | |
| $4^{III}$ | | | 3.4~3.8(m) | |
| $5^{III}$ | | | | |
| $6^{III}$ | | | | |
| $1^{IV}$ | | 5.60(d,J = 1.5 Hz) | | |
| $2^{IV}$ | | | | |
| $3^{IV}$ | | | | |
| $4^{IV}$ | | 3.4~3.8(m) | | |
| $5^{IV}$ | | | | |
| $6^{IV}$ | | | | |

TABLE 2

$^{13}$CNMR data 1, 2, 3, 4

| | 1st | 2nd | 3rd | 4th |
|---|---|---|---|---|
| 2 | 158.4 | 159.5 | 160.2 | 158.7 |
| 3 | 134.7 | 137.0 | 136.4 | 135.1 |
| 4 | 178.4 | 180.3 | 180.2 | 178.7 |
| 5 | 161.6 | 164.5 | 163.7 | 162.1 |
| 6 | 99.7 | 67.3 | 100.8 | 99.7 |
| 7 | 165.5 | 167.0 | 166.7 | 165.7 |
| 8 | 94.8 | 95.9 | 95.8 | 94.8 |
| 9 | 157.6 | 159.5 | 159.4 | 157.8 |
| 10 | 104.6 | 106.8 | 105.5 | 104.9 |
| 1' | 122.1 | 126.5 | 123.6 | 122.0 |
| 2' | 115.8 | 133.0 | 133.2 | 132.0 |
| 3' | 144.9 | 118.5 | 116.9 | 115.9 |
| 4' | 149.0 | 162.0 | 162.2 | 160.9 |
| 5' | 117.1 | 117.5 | 116.9 | 115.9 |
| 6' | 123.0 | 133.5 | 133.2 | 132.0 |
| $1^I$ | 103.7 | 105.3 | 106.5 | 104.3 |
| $2^I$ | 74.6 | 76.7 | 76.5 | 75.0 |
| $3^I$ | 76.9 | 79.1 | 79.0 | 77.5 |
| $4^I$ | 70.1 | 72.6 | 72.2 | 70.4 |
| $5^I$ | 77.1 | 78.2 | 77.9 | 77.1 |
| $6^I$ | 67.6 | 68.5 | 69.6 | 67.9 |
| $1^{II}$ | 101.4 | 103.2 | 103.1 | 101.7 |
| $2^{II}$ | 70.9 | 73.1 | 72.1 | 71.2 |
| $3^{II}$ | 71.3 | 72.8 | 83.8 | 71.8 |
| $4^{II}$ | 72.7 | 74.7 | 73.4 | 73.1 |
| $5^{II}$ | 68.9 | 70.7 | 70.2 | 69.0 |
| $6^{II}$ | 17.4 | 18.7 | 18.7 | 17.7 |
| $1^{III}$ | | | 106.4 | |
| $2^{III}$ | | | 76.3 | |
| $3^{III}$ | | | 78.4 | |
| $4^{III}$ | | | 71.8 | |
| $5^{III}$ | | | 78.4 | |
| $6^{III}$ | | | 63.0 | |
| $1^{IV}$ | | 100.5 | | |
| $2^{IV}$ | | 73.2 | | |
| $3^{IV}$ | | 73.0 | | |
| $4^{IV}$ | | 74.7 | | |
| $5^{IV}$ | | 71.9 | | |
| $6^{IV}$ | | 18.9 | | |

When the above first, second, third and fourth components and thearubigin fraction were subjected to the organoleptic test described below, all participants (13) felt either "distasteful" or "bitter" for thearubigin fraction, while only three participants felt either "distasteful" or "bitter" for the first, second, third and fourth components. It is noted that twelve participants felt "good" and six participants felt "salty" for the control.

(Measurement of Neutralizing Activity Against Bacterial Toxin)

Four-week-old male and female ddY strain mice were bred in group and fed with a diet and drinking water ad libitum, and the preparations of phrenic nerve-diaphragm muscles of three to eight-month-old mice were prepared according to the method by Buelbring for rats. The isolated muscle was cut along the direction of muscle fiber with a width of about 1 cm, leaving the input part of the phrenic nerve at the center, and this preparation was used for measurement of twitch contraction.

Figure 2:
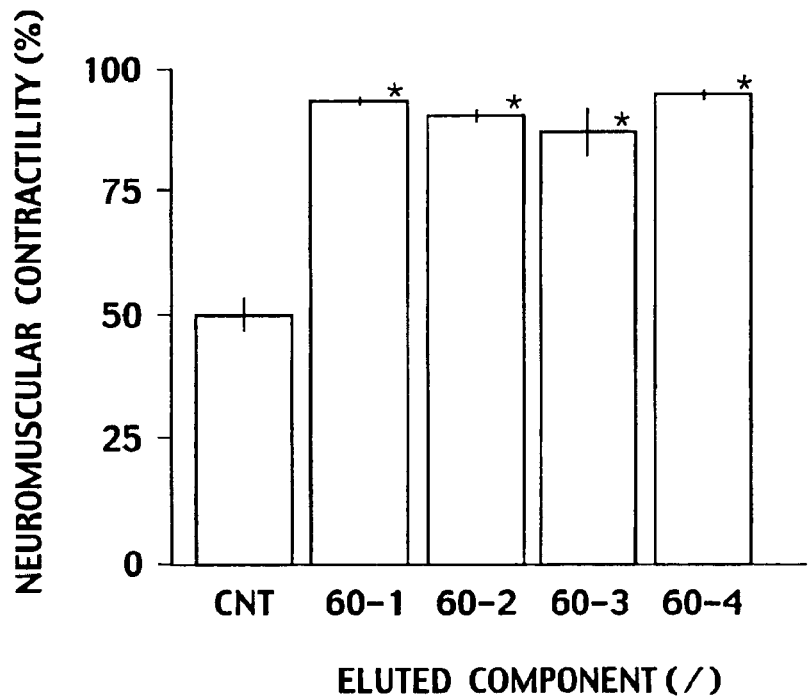
FIG. 2 is a graph showing neuromuscular contractility observed for each of eluted components derived from 60% methanol eluate.

*Botulinum* neurotoxin type A (15 μg/15 μL, made by Wako Jun-yaku Industries, Ltd. of Japan) and a sample solution for measurement of *botulinum* neurotoxin-neutralizing activity, i.e. eluted matter in physiologic saline (sample concentration: 1.5 μg/20 μL saline), were mixed and added to Krebs-Ringer solution. For the control, physiologic saline was used in place of the sample solution. Here, the final concentration of the neurotoxin after addition was made to be 1.5 nM. Into this solution, the preparation for measurement of twitch contraction isolated from the mouse was added. A microelectrode made of glass was repeatedly inserted into the motor nerve ending of the preparation, and the neutralization activity in FIG. 1 was evaluated using the terminal potential elicited by electric stimulation of the phrenic nerve trunk as an index. The neuromuscular contractility in FIG. 2 was determined by adding the preparation into each of the sample solution at the same time, measuring the neuromuscular contraction which was gradually decreased by toxication, and evaluating the value of neuromuscular contraction for each sample solution when the contraction for the control was reduced to 50% of that before the addition.

(Organoleptic Test)

A sterile saline solution containing each sample for measurement of *botulinum* toxin-neutralizing activity at 40 g/L was prepared. At this time, sonication was carried out for 20 minutes to facilitate the sample dissolution. Into this solution was added raw ham at the ratio of 500 g/L, which was kept soaked therein for one week in a refrigerator (4 degrees C.) and then drained to prepare the sample for organoleptic test. As a control sample, ham soaked in a sterile solution of saline not containing black tea extract was prepared.

Thirteen subjects were recruited for the test, and they had taste tests with saccharose, salt, citric acid and quinine as the preliminary test before they put the sample into their mouths with eyes covered with a sleep shade, masticated for one minute and then reported the gustatory sense they felt.

As described above, the present invention provides clostridial toxin-neutralizing agents which can be added to food without affecting its flavor or giving a bitter taste and the like, and can preferably neutralize *botulinum* toxins and the like, thereby contributing to the safety of food to a great extent.

It must be understood that the invention is in no way limited to the above embodiments and that many changes may be brought about therein without departing from the scope of the invention as defined by the appended claims.

What is claimed is:

1. A flavonol glycoside having a chemical structure which is expressed by the following formula, where -rha represents a rhamnosyl group, and -glc-rha represents a rutinosyl group 2. A neutralizing agent for a *clostridium* bacterial neurotoxin, comprising at least one of a flavonol glycoside (A) and a flavonol glycoside (B):

the flavonol glycoside (A) having a flavone skelton which has two hydroxyl groups at the 5 and 7 positions, at least one hydroxyl group bonding at either one of the 3', 4' and 5' positions, and an ether linkage forming glycoside at the 3 position with a carbohydrate chain containing a rutinose skelton, and the flavonol glycoside (B) having a flavone skelton which has two hydroxyl groups at the 5 and 7 positions, an ether linkage forming glycoside at the 4' position with a carbohydrate chain containing a rhamnose skelton, and an ether linkage forming glycoside at the 3 position with a carbohydrate chain containing a rutinose skelton.

3. The neutralizing agent of claim 2, wherein the flavonol glycoside (A) includes at least one component which is selected from the group consisting of rutin, nicotiflorin and kaempfetrin.

4. The neutralizing agent of claim 2, wherein the bacterial neurotoxin is a neurotoxin of *Clostridium bothulinum*.

5. The neutralizing agent of claim 2, wherein the bacterial neurotoxin is a neurotoxin of *Clostridium tetani*.

6. A method for preparing a neutralizing agent for a *clostridium* bacterial neurotoxin, comprising:

separating the thearubigin fraction of black tea extract by elution with methanol/water solvent using a reverse phase liquid chromatography; and collecting a fraction eluted with methanol/water solvent containing 40% methanol and/or a fraction eluted with methanol/water solvent containing 60% methanol.

7. A method for preparing a neutralizing agent for a *clostridium* bacterial neurotoxin, comprising:

purifying the thearubigin fraction of black tea extract by elution separation of the thearubigin fraction with methanol/water solvent using the reverse phase liquid chromatography.

8. The preparation method of claim 6, comprising:

extracting black tea leaves with aqueous acetone solution to obtain extract solution, and removing acetone and water from the extract solution to obtain the black tea extract; and dispersing the black tea extract in water, subjecting the aqueous dispersion to sequential partition extraction with n-hexane, chloroform, ethyl acetate and n-butanol in order, and collecting the n-butanol extract to obtain the thearubigin fraction.

9. The preparation method of claim 7, comprising:

extracting black tea leaves with aqueous acetone solution to obtain extract solution, and removing acetone and water from the extract solution to obtain the black tea extract; and dispersing the black tea extract in water, subjecting the aqueous dispersion to sequential partition extraction with n-hexane, chloroform, ethyl acetate and n-butanol in order, and collecting the n-butanol extract to obtain the thearubigin fraction.

10. The neutralizing agent for a *clostridium* bacterial neurotoxin, produced by the preparation method of claim 6.

11. The neutralizing agent for a *clostridium* bacterial neurotoxin, produced by the preparation method of claim 7.

* * * * *